Figure 2:
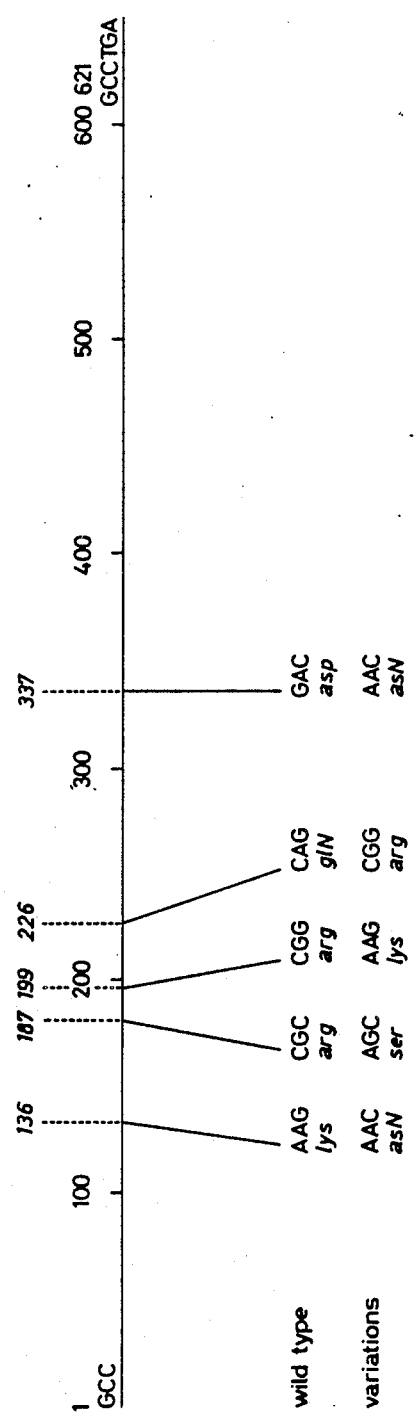

United States Patent [19]
Verrips et al.

[11] Patent Number: 4,891,316
[45] Date of Patent: Jan. 2, 1990

[54] DNA SEQUENCES ENCODING THE VARIOUS ALLELIC FORMS OF MATURE THAUMATIN, AND CLONING VEHICLES, ETC.

[75] Inventors: Cornelis T. Verrips, Maassluis; Adrianus M. Ledeboer, Rotterdam; Luppo Edens, Maassluis; Robert Klok, Vlaardingen; Jan Maat, Monster, all of Netherlands

[73] Assignee: Unilever Patent Holdings B.V., Netherlands

[21] Appl. No.: 742,139

[22] Filed: Jun. 7, 1985

Related U.S. Application Data

[63] Continuation of Ser. No. 329,829, Dec. 11, 1981, abandoned.

[30] Foreign Application Priority Data

Dec. 12, 1980 [GB] United Kingdom ............... 8039855

[51] Int. Cl.$^4$ .................... C12P 21/02; C12P 21/00; C12P 19/34; C12N 15/00; C12N 1/20; C07H 21/04
[52] U.S. Cl. .................................... 435/69.1; 435/91; 435/172.1; 435/172.3; 435/320; 435/252.33; 536/27; 935/11; 935/29; 935/73
[58] Field of Search ............... 435/68, 70, 91, 172.3, 435/253, 317, 172.1, 317.1, 320; 536/27; 935/11, 29, 73

[56] References Cited

U.S. PATENT DOCUMENTS 4,237,224 12/1980 Cohen .................................... 435/68
4,321,365 3/1982 Wu et al. ............................... 435/91
4,336,336 6/1982 Silhavy et al. ......................... 435/68

FOREIGN PATENT DOCUMENTS 1565190 4/1980 United Kingdom .

OTHER PUBLICATIONS

Nature, vol. 284, 5758, Apr. 24, 1980.
Nature, vol. 281, Oct. 18, 1979, pp. 544–548.
Eur. J. Biochem., 1979, 96/1, 193–204, (Iyengar et al.).
Nucleic Acids Synthesis, Symposium Series, No. 7, Proceedings of the Int'l Symposium on Chemical Synthesis of Nucleic Acids, edited by Koster, IRL Press, Aug. (1980), Narang et al., pp. 377–385.
F. Lee et al., J. Mol. Biol. 121, 193–217 (1978).
K. Bertrand et al., Science, 189, 22–26 (1975).
K. S. Kirby (1965) Biochem. J. 96, 266–269.
Wiegers & Hilz (1972) FEBS Letters 23, 77–82.
Aviv et al., (1972) Proc. Natl. Acad. Sci. USA 69, 1408–1412.
Davies et al., (1973), J. Virol. 12, 1434–1441.
Buell et al., J. Biol. Chem. 253, 2471–2482 (1978).
Davies et al., Gene 10, 205–218 (1980).
Roychoudury et al., Nucleic Acids Research 3, 863–877 (1976).
Birnboim et al., Nucleic Acids Research, 7, 1513–1523 (1979).
Williams et al., Cell 17, 903–913 (1979).
Maxam et al., in Methods in Enzymology, L. Grossman and K. Moldave, Editors, New York, Acad. Press, 1980 vol. 65(1), pp. 499–560.
J. Maat et al., Nucleic Acids Research 5, 4537–4545 (1978).
Zimmern et al., Proc. Natl. Acad. Sci. USA, 75, 4257–4261 (1978).
Backman et al., Cell 13, 65–71 (1978).
Hallewell et al., Gene 9, 27–47 (1980).
Itakura et al., Expression in *Escherichia coli* of a Chemically Synthesized Gene for the Hormone Somatostain, Science, vol. 198, 1056 (1977).
George et al., High–Level Expression in *Escherichia coli* of Biologically Active Bovine Growth Hormone, DNA, vol. 4, No. 4, 1985, pp. 73 and 74.

(List continued on next page.)

*Primary Examiner*—James Martinell
*Attorney, Agent, or Firm*—Cushman, Darby & Cushman

[57] ABSTRACT

The invention relates to DNA sequences encoding the various allelic forms of mature thaumatin, and cloning vehicles comprising said DNA sequences and their use in transforming microorganisms.

13 Claims, 8 Drawing Sheets

OTHER PUBLICATIONS de Vos et al., Proc. Natl. Acad. Sci. USA, vol. 82, pp. 1406–1409, Mar. 1985; Three-Dimensional Structure of Thaumatin I, an Intensely Sweet Protein.

van Wezenbeek et al.; Gene, 11 (1980) 129–148, Eleavier/North Holland Biomedical Press; Nucleotide Sequence of the Filamentous Bacteriophage M13 DNA Genome: Comparison with Phage fd.

Stauffer et al.: Proc. Natl. Acad. Sci. USA 75, 4833 (1978).

Roberts et al.; Proc. Natl. Acd. Sci. USA 76: 760 (1979).

*Henderson's Dictionary of Biological Terms,* Holmes, 1979, Van Nostrand Reinhold Company, New York, p. 376.

Helling et al., "The Molecular Cloning of Genes-General Procedures", in *Genetic Engineering,* 1978, Chakrabarty (ed.), CRC Press, Boca Raton, Fla., pp. 1–30.

Iyengar et al.: Chem. Abstr. 91, 118895c (1979).

Messing: Recombinant DNA Technical Bulletin, vol. 2, pp. 43–48 (1979).

Maniatis et al.: *Molecular Cloning: A Laboratory Manual,* Cold Spring Harbor Laboratory, 1982, pp. 197–198.

Fig.1.

```
1
ALA THR PHE GLU ILE VAL ASN ARG CYS SER TYR THR VAL TRP ALA ALA ALA SER LYS GLY
GCC ACC TTC GAG ATC GTC AAC CGC TGC TCC TAC ACC GTG TGG GCG GCC GCC TCC AAA GGC

61
ASP ALA ALA LEU ASP ALA GLY GLY ARG GLN LEU ASN SER GLY GLU SER TRP THR ILE ASN
GAC GCC GCC CTG GAC GCC GGC GGC CGC CAG CTC AAC TCG GGA GAG TCC TGG ACC ATC AAC

121
VAL GLU PRO GLY THR LYS GLY GLY LYS ILE TRP ALA ARG THR ASP CYS TYR PHE ASP ASP
GTA GAA CCC GGC ACC AAG GGT GGC AAA ATC TGG GCC CGC ACC GAC TGC TAT TTC GAC GAC

181
SER GLY ARG GLY ILE CYS ARG THR GLY ASP CYS GLY GLY LEU LEU GLN CYS LYS ARG PHE
AGC GGC CGC GGC ATC TGC CGG ACC GGC GAC TGC GGC GGC CTC CTC CAG TGC AAG CGC TTC

241
GLY ARG PRO PRO THR THR LEU ALA GLU PHE SER LEU ASN GLN TYR GLY LYS ASP TYR ILE
GGC CGG CCG CCC ACC ACG CTG GCG GAG TTC TCG CTC AAC CAG TAC GGC AAG GAC TAC ATC

301
ASP ILE SER ASN ILE LYS GLY PHE ASN VAL PRO MET ASP PHE SER PRO THR THR ARG GLY
GAC ATC TCC AAC ATC AAA GGC TTC AAC GTG CCG ATG GAC TTC AGC CCG ACC ACG CGC GGC

361
CYS ARG GLY VAL ARG CYS ALA ALA ASP ILE VAL GLY GLN CYS PRO ALA LYS LEU LYS ALA
TGC CGC GGG GTG CGG TGC GCC GCC GAC ATC GTG GGG CAG TGC CCG GCG AAG CTG AAG GCG

421
PRO GLY GLY GLY CYS ASN ASP ALA CYS THR VAL PHE GLN THR SER GLU TYR CYS CYS THR
CCG GGC GGT GGT TGC AAC GAT GCG TGC ACC GTG TTC CAG ACG AGC GAG TAC TGC TGC ACC

481
THR GLY LYS CYS GLY PRO THR GLU TYR SER ARG PHE PHE LYS ARG LEU CYS PRO ASP ALA
ACG GGG AAG TGC GGG CCG ACG GAG TAC TCG CGC TTC TTC AAG AGG CTT TGC CCG GAC GCG

541
PHE SER TYR VAL LEU ASP LYS PRO THR THR VAL THR CYS PRO GLY SER SER ASN TYR ARG
TTC AGT TAT GTC CTG GAC AAG CCA ACC ACC GTC ACC TGC CCC GGC AGC TCC AAC TAC ACG

601
VAL THR PHE CYS PRO THR ALA
GTC ACT TTC TGC CCT ACT GCC
```

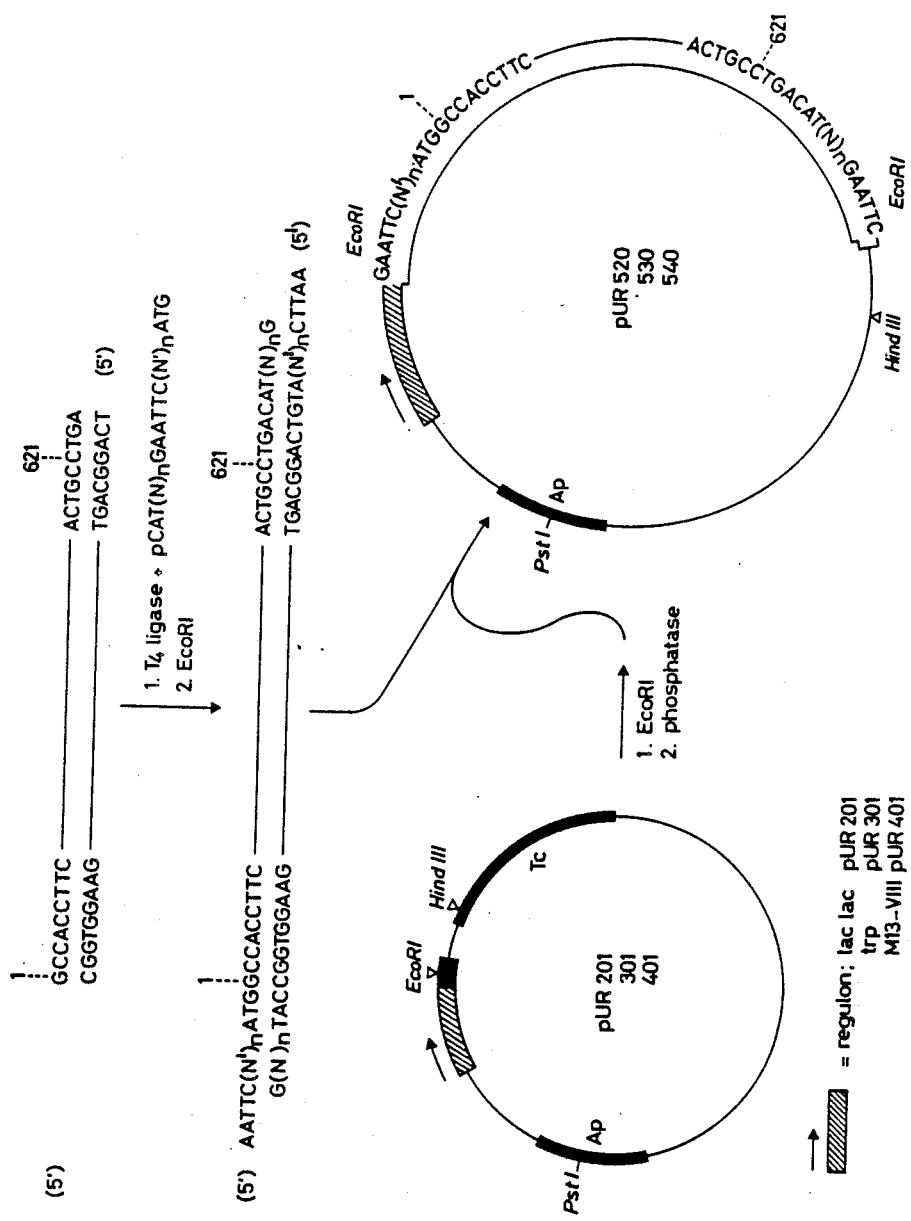

DNA SEQUENCES ENCODING THE VARIOUS ALLELIC FORMS OF MATURE THAUMATIN, AND CLONING VEHICLES, ETC.

This is a continuation of application Ser. No. 329,829, filed Dec. 11, 1981, which was abandoned upon the filing hereof.

The present invention relates to DNA sequences encoding the various allelic forms of mature thaumatin, and cloning vehicles comprising said DNA sequences and their use in transforming microorganisms.

Thaumatin is a protein originating from the arils of the fruit of *Thaumatococcus daniellii*. Thaumatin is, on a weight basis, 1600 times sweeter than sucrose and on a molecular basis $10^5$ times sweeter than sucrose. In Western society overconsumption of sugar causes a number of health problems. Therefore, many attempts have been made to substitute low caloric sweeteners for sugar. However, several of these have recently been prohibited in view of possible side-effects. There is thus a need for a natural low caloric sweetener and for an economical process of producing such a sweetener. Recent advances in molecular biology have enabled the introduction of structural genes coding for specific eukaryotic proteins into microbial host cells and expressing said genes in the transformed host cells, thereby producing the desired protein.

Many genes of eukaryotic origin which in their natural state encode proteins in their unprocessed forms cannot be applied directly in recombinant DNA molecules because natural genes contain DNA sequences called introns, which are not contained in the messenger RNA (mRNA). The information located on these introns is removed in eukaryotic cells before the translation process of the mRNA. As far as Applicants are aware, bacteria are unable to excise such introns at RNA level and therefore it is necessary to remove the genetic information located on these introns at RNA level before the natural gene of eukaryotes can be used in prokaryotic host cells.

In microbial host cells, that have the capability of excising introns at mRNA level the natural genes can in principle be applied, provided that they are brought under control of regulons that are effective in said microbial host cells.

In the present invention use is made of recombinant DNA techniques that introduce the genetic information of eukaryotic, particularly of plant, origin, in such a state that expression occurs effectively in microbial, particularly in bacterial host cells.

For a better understanding of the invention the most important terms used in the description will be defined:

A regulon is a DNA sequence consisting of a promotor and operator region.

Structural genes are DNA sequences which encode through a template (mRNA) a sequence of amino acid characteristic of a specific polypeptide.

A promoter is a DNA sequence within the regulon to which RNA polymerase binds for the initiation of the transcription.

An operator is a DNA sequence within the regulon to which a repressor protein may bind, thus preventing RNA polymerase from binding to the adjacent promotor.

An inducer is a substance which deactivates a repressor protein, freeing the operator and permitting RNA polymerase to bind to the promoter and start transcription.

By mature thaumatin is meant one of the allelic forms of the fully processed protein (FIG. 1).

Cloning vehicle. A non-chromosomal double-stranded DNA, plasmid or phage, comprising a DNA sequence (intact replicon) that allows self-replication after transformation into suitable host cells.

Phage or bacteriophage. Bacterial virus which can replicate in a suitable bacterial host cell.

Reading frame. The grouping of triplets of nucleotides (codons) into such a frame that at mRNA leve a proper translation of the codons into the polypeptide takes place.

Transcription. The process of producing RNA from a gene.

Translation. The process of producing a polypeptide from mRNA.

Expression. The process undergone by a structural gene to produce a polypeptide. It is a combination of many processes, including at least transcription and translation.

By mature thaumatin gene is meant the double-stranded DNA sequence having exactly the same information content (sequence of codons) as that part of the messenger RNAs coding for the various allelic forms of thaumatin in their fully processed (mature) form. For reasons of convenience only one strand of ds DNA is given in the text and figures.

According to the invention there is provided a recombinant plasmid comprising:

(i) structural genes coding for the various allelic forms of thaumatin and particularly mature thaumatin, according to FIGS. 1 and 2

(ii) specific DNA sequences which regulate the expression of said structural genes. These specific DNA sequences consist of either an inducible or a constitutive regulon. A preferred inducible regulon consists of a double lac UV5 system as described by D. V. Goeddel et al., Nature 281, 544–548 (1979).

Another preferred inducible regulon is a constituent of the tryptophan system described by F. Lee et al., J. Mol. Biol. 121, 193–217 (1978) and K. Bertrand et al., Science 189, 22–26 (1975). Applicants have modified this tryptophan system to obtain a more adequate system according to FIG. 3. In this modified system the information coding for the trp attenuator protein is eliminated while maintaining the ribosome binding site.

The recombinant plasmid according to the invention may comprise DNA sequences consisting of a modified promoter/ribosome-binding site of gene VIII of bacteriophage M13, fd of fl [P. M. G. F. van Wezenbeek et al., Gene 11, 129–148 (1980)], which, as far as Applicants are aware, were never used before for the expression of eukaryotic genes.

In the recombinant plasmid according to the invention the regulon may be either directly linked to the structural gene or indirectly through a novel start codon and EcoRI-site containing DNA linker comprising the nucleotide sequence $CAT(N)_nGAATTC(N')_nATG$, wherein $n=0, 1, 2$ or $3$, and N and N' are any of the nucleotides A, T, G or C, with the proviso that in the double-stranded structure N and N' are such that a rotational symmetrical structure is present.

By a rotational symmetrical structure is meant that where N is e.g. represented by A, N' should be represented by the complementary base T.

In some instances it turned out that the yield of expression improved when the sequence AATT between the regulon and the structural gene has been eliminated.

The microbial cloning vehicles containing the structural genes encoding the various allelic forms of the mature (fully processed) thaumatin according to the invention are obtained and the various thaumatins are produced by performing a number of steps, the most essential of which are:

(1) isolation and purification of the messenger RNA (mRNA) of thaumatin;
(2) conversion of this mRNA into double-stranded DNA (ds DNA);
(3) construction of ds DNA having a poly-dC tail;
(4) incorporation of the ds DNA-poly-dC molecules in endonuclease PstI-cleaved, and poly-dG-tailed plasmid pBR 322 DNA;
(5) transformation and clone selection;
(6) determination of the nature of the insert by RNA/DNA hybridization and in vitro translation;
(7) double-checking the nature of the inserts by DNA- and RNA-sequence analysis;
(8) producing DNA encoding the mature fully processed thaumatin;
(9) construction of plasmids comprising specific transcription regulating DNA sequences, and chemical synthesis of DNA-linkers and -primers;
(10) construction of plasmids comprising a constitutive or inducible regulon and the ligated thaumatin gene; and transformation of E.coli with said plasmids;
(11) culturing of E.coli cells containing said recombinant plasmids and detection and isolation of the thaumatin.

The following detailed description will illustrate the invention.

1. Isolation and purification of mRNA (thaumatin)

Isolated arils of *Thaumatococcus, daniellii* were ground under liquid nitrogen. After protein extraction with phenol, a selective precipitation of the RNAs with LiCl was performed following the procedures described by K. S. Kirby (1965) Biochem. J. 96, 266–269, U. Wiegers and H. Hilz (1972) FEBS Letters 23, 77–82. Poly-A containing messenger RNA was recovered by several passages over oligo-dT-cellulose columns and from this messenger mixture the thaumatin-encoding mRNA was isolated by polyacrylamide gel electrophoresis. This was checked by translation of the mRNA in the wheat germ system as described by H. Aviv and P. Leder (1972), Proc. Natl. Acad. Sci. U.S.A. 69, 1408–1412 and J. W. Davies and P. Kaesberg (1973), J. Virol. 12, 1434–1441.

2. Conversion of thaumatin mRNA into double-stranded DNA

The purified thaumatin mRNA was copied with AMV reverse transcriptase to yield a single-stranded DNA molecule, according to the procedure described by G. N. Buel et al., J. Biol. Chem. 253, 2471–2482 (1978). This cDNA subsequently converted into a double-stranded molecule by E.coli DNA-polymerase, according to the procedure described by A. R. Davis et al., Gene 10, 205–218 (1980). The loop structure of the double-stranded DNA copy was removed by $S_1$-nuclease digestion.

3. Construction of double-stranded DNA with poly-dC tails

DNA molecules of the desired length were obtained by polyacrylamide gel-electrophoresis, extracted from the gel and tailed with poly-dC by terminal transferase according to the procedure described by R. Roychoudhury et al., Nucleic Acids Research 3, 863–877 (1976).

4. Integration of the ds DNA-dC molecules in plasmid pBR 322

Plasmid pBR 322 was treated with restriction endonuclease Pst I, that cleaves the plasmid at a recognition site that lies in the β-lactamase gene, whereafter the linearized DNA of pBR 322 was supplied with poly-dG tails by terminal transferase. The poly-dC tailed DNA molecules were annealed to the poly-dG tailed plasmid pBR 322.

5. Transformation and clone selection

The plasmids thus obtained were transferred into $CaCl_2$-treated *E.coli* cells. After transformation cells containing hybrid plasmid DNA molecules were selected on their resistance to tetracycline. Positive colonies were screened for plasmids with large inserts by a combination of a rapid plasmid extraction procedure as outlined by H. C. Birnboim and J. Doly, Nucleic Acids Research, 7, 1513–1523 (1979) and an endonuclease Pst-I-digestion of the isolated DNA.

6. Determination of the nature of the inserts (I). Hybridization/in vitro translation.

From the selected clones 10 μg plasmid DNA were isolated, which subsequently were bound to diazotated (DMB) paper discs. The immobilized plasmid DNA molecules were used in an hybridization/in vitro translation procedure as outlined by J. G. Williams et al., Cell 17, 903–913 (1979) in order to determine the nature of the DNA insert.

7. Determination of the nature of the inserts (II) by DNA/RNA sequence analysis

The nucleotide sequence analysis of the thaumatin inserts was performed by the chemical degradation procedure as outlined by A. M. Maxam and W. Gilbert in Methods in Enzymology, L. Grossman and K. Moldave editors, New York, Acad. Press, 1980, Vol. 65 (1), pages 499–560 and by the dideoxy/nick translation procedure as outlined by J. Maat and A. J. H. Smith, Nucleic Acids Research, 5, 4537–4545 (1978). Further information on the nucleotide sequence of the thaumatin mRNA was derived indirectly by primed synthesis by AMV-reverse transcriptase on the thaumatin mRNA template in the presence of chain terminating inhibitors, as outlined by D. Zimmern and P. Kaesberg, Proc. Natl. Acad. Sci. U.S.A. 75, 4257–4261 (1978). This screening yielded inter alia plasmid pUR 100 containing an almost complete copy of thaumatin mRNA.

8. Construction of DNA encoding the mature, fully processed thaumatin

Figure 4:
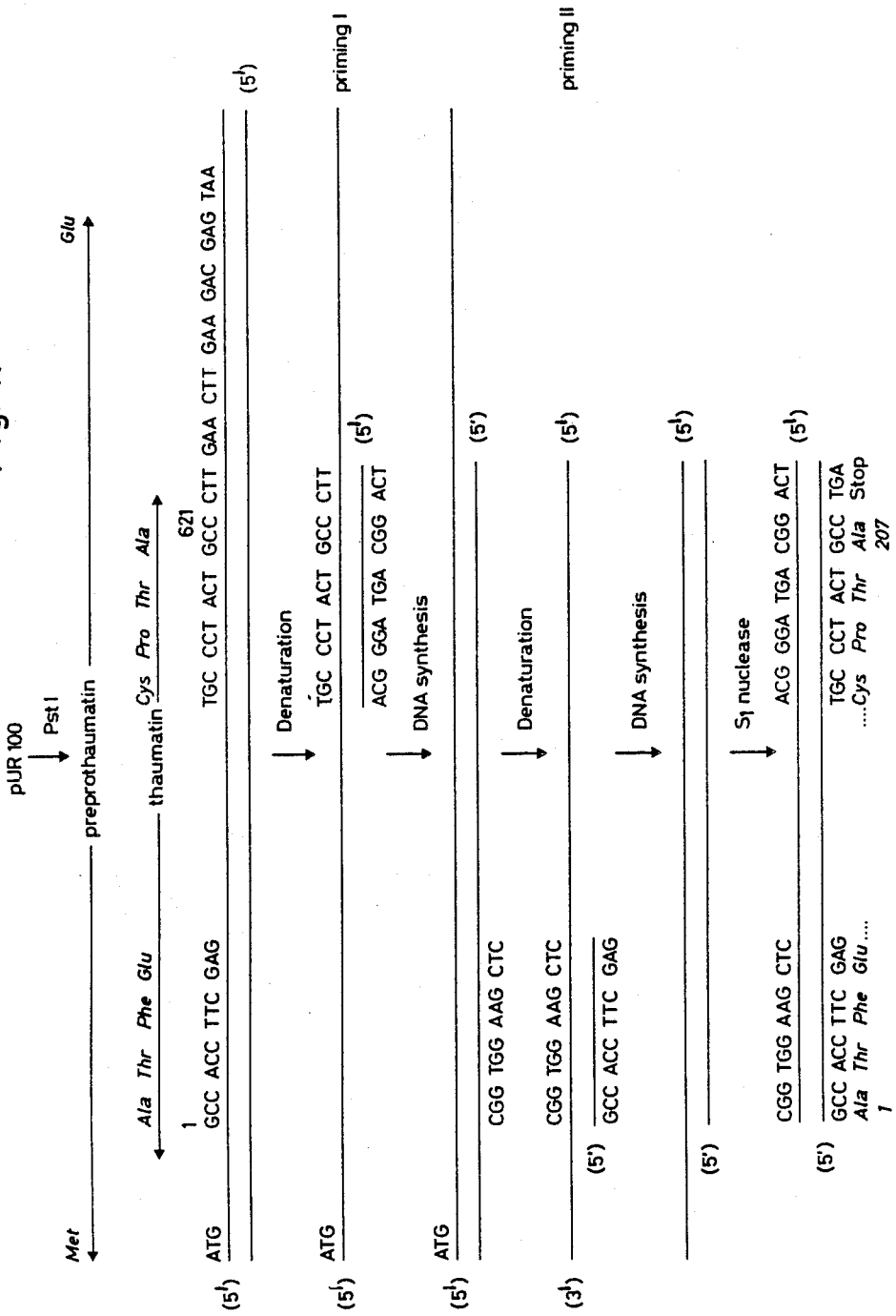

Single-stranded DNA was obtained by exonuclease III treatment of pUR 100 as outlined by A. J. H. Smith, Nucleic Acids Res., 6, 831–848 (1979) or by cloning in M13, as outlined by B. Gronenborn and J. Messing, Nature 272, 375–377 (1978). Single-stranded DNA with the same polarity as the thaumatin mRNA was used as template for complementary DNA synthesis with the chemically synthesized oligonucleotide (5') pTCAGG-CAGTAGGGCA$_{OH}$(3') serving as a primer; after heat-denaturation of the double-stranded DNA, the complementary DNA served as template for DNA synthesis by using the chemically synthesized oligonucleotide (5') pGCCACCTTCGAG$_{OH}$(3') as a primer. This double-stranded DNA was then treated with S1 nuclease. The construction of the mature thaumatin gene is illustrated in FIG. 4.

9a. Construction of a plasmid pUR 201

Figure 5:
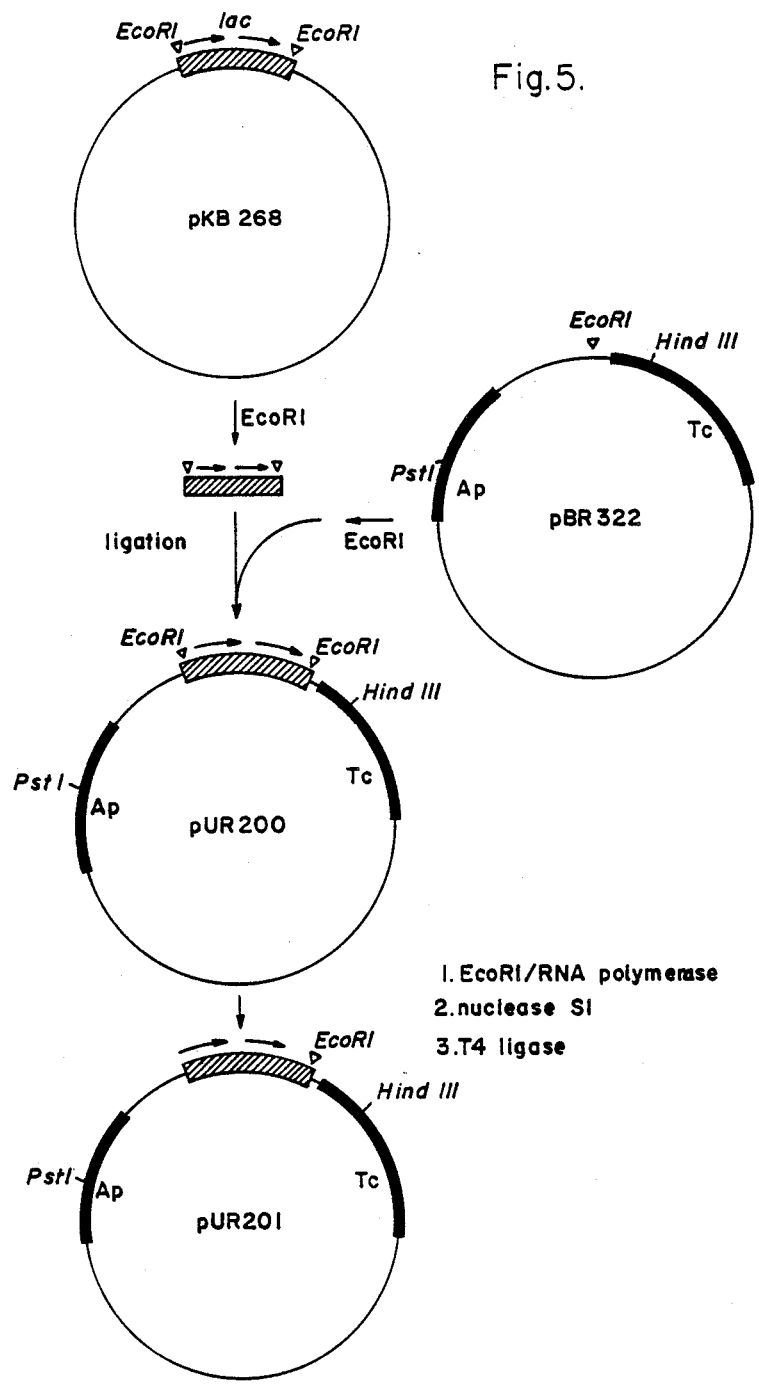

A fragment containing 285 base pairs comprising the double lac regulon (lac UV5) was obtained by restriction endonuclease EcoRI cleavage of pKB 26B, (K. Backman and M. Ptashne, Cell 13, 65–71 (1978)). This fragment was ligated in the EcoRI site of pBR 322 DNA. Plasmid DNA with the lac regulon in the right orientation (FIG. 5) was partly cleaved by EcoRI in the presence of *E.coli* RNA polymerase. The EcoRI cleavage site most distant from the restriction endonuclease Hind III cleavage site was preferentially attacked. The linearized DNA was treated with S1 nuclease, purified by agarose gel electrophoresis, circularized by ligation with T4 DNA-ligase and subsequently used to transform *E.coli*. From the tetracycline-resistant transformants pUR 201 with the correct structure (FIG. 5) was obtained.

9b. Construction of plasmid pUR 301

Figure 3:
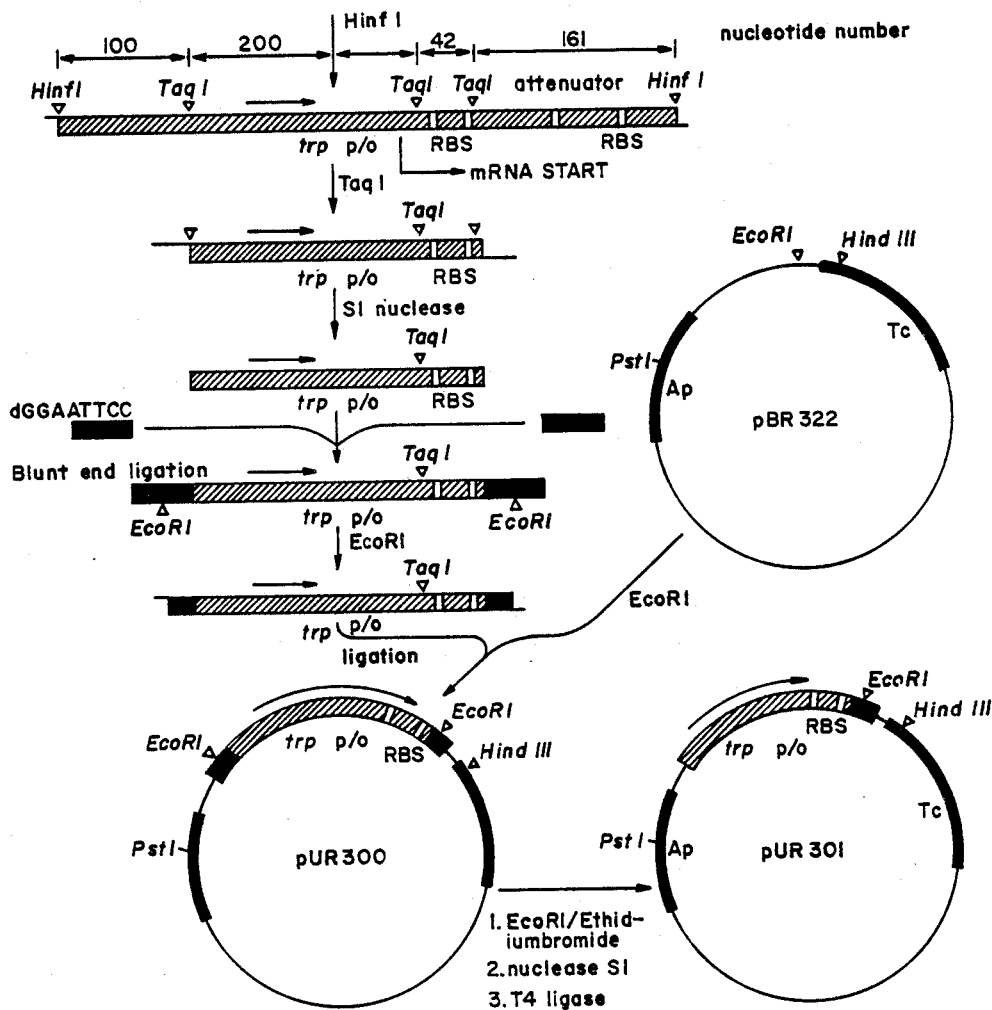

A DNA fragments of about 510 base pairs was obtained by restriction endonuclease Hinf I cleavage of ptrp ED5, (R. A. Hallewell and S. Emtage, Gene 9, 27–47 (1980)). This fragment was cleaved with restriction endonuclease Taq I in the presence of *E.coli* RNA polymerase. The Taq I site in the trp regulon (described by K. Bertrand et al., Sience 189, 22–26 (1975) and F. Lee et al., J. Mol. Biol. 121, 193–217 (1978)) was selectively protected, thus yielding a fragment containing 234 base pairs comprising the trp regulon (FIG. 3). This fragment was then treated with S1 nuclease, blunt-end ligated with the EcoRI-linker (5') pGGAATTCC$_{OH}$ (3'), cut with EcoRI and subsequently cloned in the EcoRI-site of pBR 322.

Plasmid pUR 300 with the trp regulon in the correct orientation (FIG. 3) was isolated. The EcoRI-cleavage site most distant from the Hind III site was removed by partial cleavage of pUR 300 DNA by EcoRI in the presence of ethidium bromide, and S1 nuclease treatment. Linear DNA molecules were recircularized by T4 DNA ligase. From the tetracycline-resistant transformants pUR 301 with the structure as outlined in FIG. 3 was obtained.

9c. Construction of Plasmid pUR 401

Figure 6:
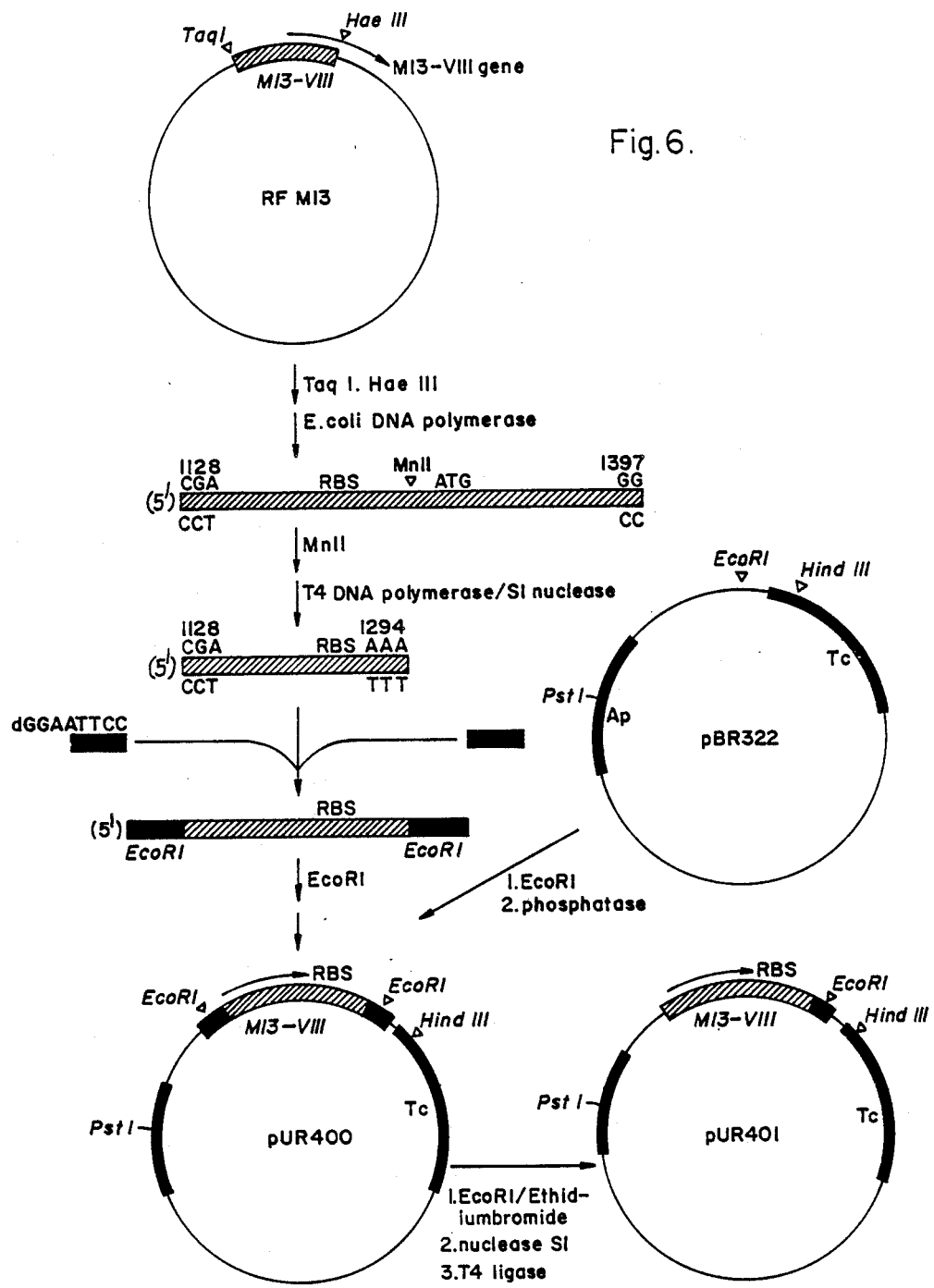

A fragment containing 270 base pairs (DNA sequence 1128–1397) was obtained by digestion of RF M13 DNA (see P. M. G. F. v. Wezenbeek et al., Gene 11, 129–148 (1980)), with the restriction endonuclease Taq I and Hae III and the Taq I site was made blunt-ended by a repair reaction with *E.coli* DNA polymerase; the fragment was subsequently partly digested with restriction enzyme MnlI. The partial products were treated with successive actions of T4 DNA polymerase and S1 nuclease and subsequently blunt-end ligated with the EcoRI-linker (5') pGGAATTCCH$_{OH}$ (3'), then treated with EcoRI and ligated in the EcoRI site of the pBR 322. By restriction enzyme analysis and DNA sequence analysis a plasmid was obtained in which the EcoRI cleavage site was located just beyond the ribosome-binding site of the M13 gene VIII DNA sequence. Applicants have found that the plasmids having the M13 regulon from nucleotide 1128 to nucleotides 1291 to 1297 were appropriate regulons for expression. The EcoRI cleavage site most distant from the Hind III site was removed essentially as described for pUR 301. The complete construction of pUR 401 is outlined in FIG. 6.

9d. Chemical synthesis of linkers and primers

The synthesis of oligodeoxynucleotides is carried out through coupling of 5'-0-levulinyldeoxynucleoside-3'-0-2,2,2-trichloroethyl-2-chlorophenyl phosphates with deoxynucleoside-3'-0-2,2,2-trichloroethyl-2-chlorophenyl phosphates. This method, which is known as the phosphotriester method (described by J. F. M. de Rooij et al., Recl. Trav. Chim. Pays-Bas 98, 537–548 (1979)), involves splitting off the trichloroethyl group by active zinc, followed by the actual coupling reaction with the help of 2,4,6-triisopropylbenzenesulphonyl-3-nitro-1,2,4-triazole. The amino groups in deoxyadenosine, deoxycytidine and deoxyguanosine are protected by a benzoyl group, a 4-methoxybenzoyl group and a benzoyl group, respectively. For the protection of the 3'-hydroxy function of the terminal nucleoside the benzoyl group is used. In the last step all protecting groups are removed through reaction with tetrabutylammonium floride and concentrated aqueous ammonia, respectively.

Figure 7:
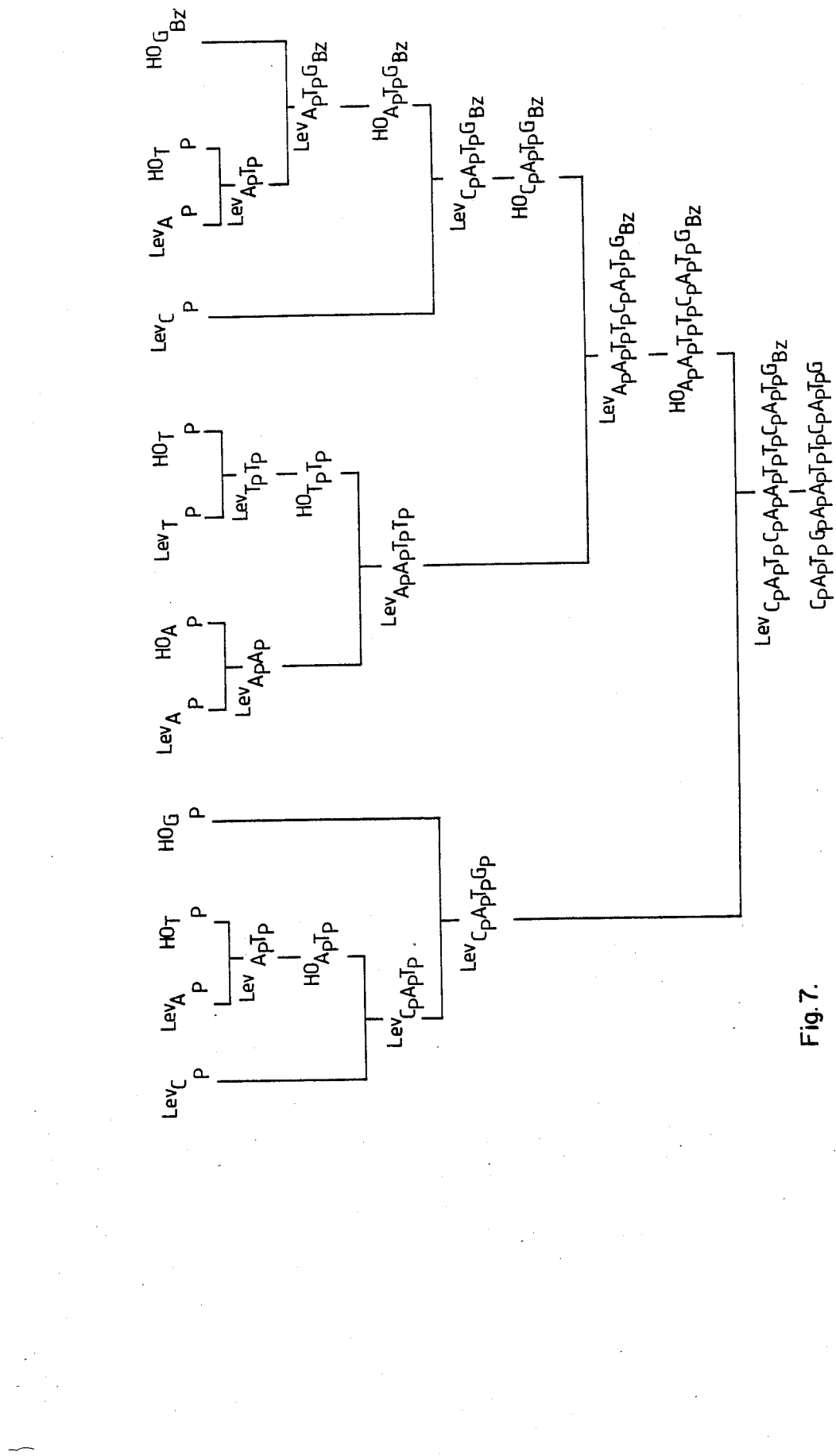

An example of the construction of the linker (5') pCATGAATTCATG$_{OH}$ (3') is given in FIG. 7.

10. Construction of expression plasmids with the mature thaumatin gene under transcription control of the double lac UV5-(pUR 520), the trp-(pUR 530) and the M13 or f1 or fd gene VIII region (pUR 540) and transformation of *E. coli* with said plasmids.

The thaumatin encoding DNA fragment described under 8 was blunt-end ligated with the synthetic EcoRI-linker (5') pCAT(N)$_n$GAATTC(N')$_n$ATG$_{OH}$ (3'), n being zero, with T4 DNA ligase, cleaved with EcoRI and subsequently ligated in the EcoRI-cleavage site of the plasmids pUR 201, pUR 301 and pUR 401, and recombinant plasmids with the thaumatin encoding insert in the orientation as illustrated in FIG. 8 were isolated after transformation of *E. coli* and selection of tetracycline-resistant transformants. In the above-described plasmids the AATT sequence originating from the chemically synthesized linkers could be deleted by cleavage of the plasmids with EcoRI in the presence of ethidium bromide; linear partials were isolated by agarose gel electrophoresis, treated with S1 nuclease and recircularized by T4 DNA ligase action.

Plasmids obtained after deletion of AATT were detected by restriction enzyme analysis.

11. Culturing of *E. coli* cells containing said recomnant plasmids and detection of the thaumatin

*E. coli* cells containing plasmids pUR 520 or pUR 530 or pUR 540 with or without the AATT sequence in the linker between the regulon and the mature thaumatin gene(s) in the correct orientation and reading frame were cultured under conditions most suitable for their growth—these culturing conditions vary with the type of plasmid present in the cells—but always in the presence of an appropriate anti-biotic to maintain selection pressure. Under these conditions the cells containing either plasmids pUR 520 or pUR 530 or pUR 540 produced considerable amounts of mature thaumatin.

The presence of the protein thaumatin was demonstrated qualitively by S.D.S. electrophoresis and by physiological tests on their sweetness and quantitatively by the enzyme linked immuno sorbent assay (ELISA).

Cells of *E. coli* strains K12(294) containing plasmids pUR 520 or pUR 530 were deposited under the Budapest Treaty on Dec. 2, 1981, at the American Type Culture Collection, 12301 Parklawn Drive, Rockville, Md., U.S.A., and have acquired the following registration numbers: ATCC 39014 and ATCC 39013, respectively.

We claim:

1. A recombinant DNA sequence selected from the group consisting of (i) a thaumatin II gene, of which the coding strand is

```
1
|
GCC ACC TTC GAG ATC GTC AAC C

-continued

```
                      541          547
                       |            |
AAG AGG CTT TGC CCG GAC GCG TTC AGT TAT GTC

CTG GAC AAG CCA ACC ACC GTC ACC TGC CCC GGC 586                 601
  |                   |
AGC TCC AAC TAC AGG GTC ACT TTC TGC

621
                                  |
                      CCT ACT GCC ,
``` and (b) variations of said thaumatin gene given in (a) which variations consist of at least one, but not more than four nucleotide replacements in said thaumatin II gene said nucleotide replacements selected from the group consisting of:

the nucleotide "G" at position 138 replaced by nucleotide "C", the nucleotide "C" at position 187 replaced by nucleotide "A", the nucleotides "CG" at positions 199–200 replaced by nucleotides "AA", the nucleotide "A" at position 227 replaced by nucleotide "G", and the nucleotide "G" at position 337 replaced by nucleotide "A", and (ii) an inducible or constitutive promoter and operator region which regulates the expression of said DNA sequence.

3. Recombinant plasmids according to claim 2, wherein said inducible promoter and operator region is a double lac UV5 system regulating the expression of said DNA sequence.

4. A bacterial culture comprising at least one microorganism containing at least one plasmid as claimed in claim 2.

5. Recombinant plasmids according to claim 2, wherein said inducible promoter and operator region is a tryptophan system consisting essentially of the trp promoter and operator region and the first ribosome binding site downstream of the promoter and operator region of the DNA sequence encoding the trp leader peptide.

6. A bacterial culture comprising *E. coli* cells containing pUR 520.

7. A bacterial culture comprising *E. coli* cells containing pUR 530.

8. A bacterial culture comprising *E. coli* cells containing a modified pUR520 differing from pUR520 in that the EcoRI site, GAATTC, located between the promoter and operator region and the thaumatin gene is replaced by GC.

9. A bacterial culture comprising *E. coli* cells containing a modified pUR530 differing from pUR530 in that the EcoRI site, GAATTC, located between the promoter and operator region and the thaumatin gene is replaced by GC.

10. A process for producing thaumatin which comprises:

(1) producing transformed *E. coli* cells by incorporating into *E. coli* cells a recombinant plasmid comprising:

(a) a DNA sequence selected from the group consisting of (i) a thaumatin II gene, of which the coding strand is

```
 1
 |
GCC ACC TTC GAG ATC GTC AAC CGC TGC TCC TAC 40                        61
           |                         |
     ACC GTG TGG GCG GCC GCC TCC AAA GGC GAC GCC

79
                     |
     GCC CTG GAC GCC GGC GGC CGC CAG CTC AAC TCG 118  121
                         |   |
     GGA GAG TCC TGG ACC ATC AAC GTA GAA CCC GGC 138                   157
               |                     |
     ACC AAG GGT GGC AAA ATC TGG GCC CGC ACC GAC 181     187        196
                        |       |          |
     TGC TAT TTC GAC GAC AGC GGC CGC GGC ATC TGC

199–200                                227
      | /                                    |
     CGG ACC GGC GAC TGC GGC GGC CTC CTC CAG TGC 235     241
       |       |
     AAG CGC TTC GGC CGG CCG CCC ACC ACG CTG GCG

274
                   |
     GAG TTC TCG CTC AAC CAG TAC GGC AAG GAC TAC 301          313
       |            |
     ATC GAC ATC TCC AAC ATC AAA GGC TTC AAC GTG 337              352          361
       |                |            |
     CCG ATG GAC TTC AGC CCG ACC ACG CGC GGC TGC

391
                                          |
     CGC GGG GTG CGG TGC GCC GCC GAC ATC GTG

421
                                          |
     GGG CAG TGC CCG GCG AAG CTG AAG GCG CCG

430
       |
     GGG GGT GGT TGC AAC GAT GCG TGC ACC GTG TTC 469              481
                  |                |
         CAG ACG AGC GAG TAC TGC TGC ACC ACG GGG

508
                                   |
     AAG TGC GGG CCG ACG GAG TAC TCG CGC TTC TTC 541         547
                                   |           |
     AAG AGG CTT TGC CCG GAC GCG TTC AGT TAT GTC

CTG GAC AAG CCA ACC ACC GTC ACC TGC CCC GGC 586                 601
       |                   |
     AGC TCC AAC TAC AGG GTC ACT TTC TGC

621
                                           |
                               CCT ACT GCC ,
``` and (ii) variations of said thaumatin II gene given in (i) which variations consist of at least one, but not more than four nucleotide replacements in said thaumatin II gene said nucleotide replacements selected from the group consisting of:
the nucleotide "G" at position 138 replaced by nucleotide "C",
the nucleotide "C" at position 187 replaced by nucleotide "A",
the nucleotides "CG" at positions 199–200 replaced by nucleotides "AA",
the nucleotide "A" at position 227 replaced by nucleotide "G", and
the nucleotide "G" at position 337 replaced by nucleotide "A", and
(b) an inducible or constitutive promoter and operator region which regulates the expression of said DNA sequence;
(2) culturing said transformed *E. coli* cells; and
(3) isolating the thaumatin produced by said transformed *E. coli* cells.

11. A process for the preparation of recombinant plasmids comprising:
(a) a DNA sequence selected from the group consisting of
(i) a thaumatin II gene, of which the coding strand is

1
|
GCC ACC TTC GAG ATC GTC AAC CGC TGC TCC TAC 40                              61
|                               |
ACC GTG TGG GCG GCC GCC TCC AAA GGC GAC GCC .

79
|
GCC CTG GAC GCC GGC GGC CGC CAG CTC AAC TCG 118 121
|   |
GGA GAG TCC TGG ACC ATC AAC GTA GAA CCC GGC 138                             157
|                               |
ACC AAG GGT GGC AAA ATC TGG GCC CGC ACC GAC 181     187             196
|       |               |
TGC TAT TTC GAC GAC AGC GGC CGC GGC ATC TGC 199-200                         227
| /                             |
CGG ACC GGC GAC TGC GGC GGC CTC CTC CAG TGC 235 241
|   |
AAG CGC TTC GGC CGG CCG CCC ACC ACG CTG GCG

274
|
GAG TTC TCG CTC AAC CAG TAC GGC AAG GAC TAC 301     313
|       |
ATC GAC ATC TCC AAC ATC AAA GGC TTC AAC GTG 337             352             361
|               |               |
CCG ATG GAC TTC AGC CCG ACC ACG CGC GGC TGC

391
                        |
CGC GGG GTG CGG TGC GCC GCC GAC ATC GTG

421
                        |
GGG CAG TGC CCG GCG AAG CTG AAG GCG CCG

430
|
GGG GGT GGT TGC AAC GAT GCG TGC ACC GTG TTC 469             481
|               |
CAG ACG AGC GAG TAC TGC TGC ACC ACG GGG

508
                |
AAG TGC GGG CCG ACG GAG TAC TCG CGC TTC TTC 541     547
                |       |
AAG AGG CTT TGC CCG GAC GCG TTC AGT TAT GTC

CTG GAC AAG CCA ACC ACC GTC ACC TGC CCC GGC 586                     601
|                       |
AGC TCC AAC TAC AGG GTC ACT TTC TGC

621
                                |
                CCT ACT GCC , and
(ii) variations of said thaumatin II gene given in (i) which variations consist of at least one, but not more than four nucleotide replacements in said thaumatin II gene said nucleotide replacements selected from the group consisting of
the nucleotide "G" at position 138 replaced by nucleotide "C",
the nucleotide "C" at position 187 replaced by nucleotide "A",
the nucleotides "CG" at positions 199–200 replaced by nucleotides "AA",
the nucleotide "A" at position 227 replaced by nucleotide "G", and
the nucleotide "G" at position 337 replaced by nucleotide "A", and
(b) an inducible or constitutive promoter and operator region which regulates the expression of said DNA sequence,
which process comprises:
(1) providing plasmids containing said inducible or constitutive promoter and operator region with an EcoRI site just downstream of said promoter and operator region,
(2) providing the 3' end of said DNA sequence with a stop codon and coupling both the 5' end of said DNA sequence and the 3' end of the stop codon connected to said DNA sequence with a linker having the nucleotide sequence (5')pCAT(N)-$_n$GAATTC(N')$_n$ATG$_{OH}$(3'), wherein n=0, 1, 2 or 3, and N and N' are any of the nucleotides A, T, G or C, with the proviso that in the double-stranded structure N and N' are such that a rotational symmetrical structure is present,
(3) treating the plasmid resulting from (1) with EcoRI,
(4) treating the coupling product resulting from (2) with EcoRI,
(5) coupling the EcoRI-treated plasmid resulting from (3) with the EcoRI-treated coupling product resulting from (4), and
(6) isolating plasmids having the right orientation of said inserted DNA sequence, which right orientation of said DNA sequence is downstream from the inducible or constitutive promoter and operator region as viewed in the 5'- to -3' direction of the polynucleotide chain.

12. A recombinant plasmid consisting of plasmid pUR520.

13. A recombinant plasmid consisting of plasmid pUR530.

* * * * *